United States Patent
Shirode et al.

(10) Patent No.: US 9,393,307 B2
(45) Date of Patent: Jul. 19, 2016

(54) CASPOFUNGIN COMPOSITION

(71) Applicant: Xellia Pharmaceuticals ApS, Copenhagen S. (DK)

(72) Inventors: Swapnil P. Shirode, Masharashtra (IN); Piyush Patel, Maharashtra (IN); Suresh Gidwani, Mumbai (IN); Neil Parikh, Irvine, CA (US); Atul Patil, Maharashtra (IN); Anita Bevetek Mochnik, Sesvetski Kraljevec (HR)

(73) Assignee: XELLIA PHARMACEUTICALS APS, Kobenhaven (DK)

( * ) Notice: Subject to any disclaimer, the term of this patent is extended or adjusted under 35 U.S.C. 154(b) by 46 days.

(21) Appl. No.: 14/547,742

(22) Filed: Nov. 19, 2014

(65) Prior Publication Data

US 2015/0072923 A1 Mar. 12, 2015

Related U.S. Application Data

(63) Continuation of application No. 13/237,193, filed on Sep. 20, 2011, now abandoned.

(60) Provisional application No. 61/384,333, filed on Sep. 20, 2010.

(51) Int. Cl.
*A01N 37/18* (2006.01)
*A61K 38/00* (2006.01)
*A61P 31/10* (2006.01)
*A61K 47/12* (2006.01)
*A61K 9/00* (2006.01)
*A61K 9/19* (2006.01)
*A61K 38/12* (2006.01)
*A61K 47/10* (2006.01)
*A61K 47/26* (2006.01)

(52) U.S. Cl.
CPC ............... *A61K 47/12* (2013.01); *A61K 9/0019* (2013.01); *A61K 9/19* (2013.01); *A61K 38/12* (2013.01); *A61K 47/10* (2013.01); *A61K 47/26* (2013.01)

(58) Field of Classification Search
None
See application file for complete search history.

(56) References Cited

U.S. PATENT DOCUMENTS

| 5,378,894 A | 1/1995 | Akar |
| 5,952,300 A * | 9/1999 | Nerurkar et al. ............... 514/3.3 |
| 2009/0170753 A1 | 7/2009 | Welz et al. |

FOREIGN PATENT DOCUMENTS

| WO | WO 91/15121 | * 10/1991 |
| WO | 2008012310 A1 | 1/2008 |
| WO | 2009002481 A1 | 12/2008 |
| WO | 2009158034 A1 | 12/2009 |
| WO | WO 2010/031602 | * 3/2010 |

OTHER PUBLICATIONS

Berg et al.; "Pharmaceutical Salts"; Journal of Pharmaceutical Sciences; 66(1); pp. 1-19 (1977).
Brittain, Harry G.; "Buffers, Buffering Agents, and Ionic Equilibria"; in Encyclopedia of Pharmaceutical Technology, Third Edition, vol. 1; James Swarbrick, ed; pp. 385-392; (2007).
Flynn, Gordon L.; "Buffers—pH Control Within Pharmaceutical Systems"; Journal of Parenteral Drug Association; 34(2); pp. 139-162; (1980).
Merck's Brief in Support of Its Motion for Summary Judgment on Sandoz's Obviousness Defense; US Dist. CT Dist of New Jersey; 10-CV-01625-SRC-PS; 29 pages; filed Sep. 12, 2011.
Shalaev et al.; "Thermophysical Properties of Pharmaceutically Compatible uffers at Sub-Zero Temperatures: Implications for Freeze-Drying"; Pharmaceutical Research; 19(2); pp. 195-200; (2002).
Sundaramurthi et al.; "pH Swing" in Frozen Solutions—Consequence of Sequential Crystallization of Buffer Components; The Journal of Physical Chemistry Letters; 1; pp. 265-268; (2010) with Supplementary Information; 5 pages).

* cited by examiner

*Primary Examiner* — Marcela M Cordero Garcia
*Assistant Examiner* — Sergio Coffa
(74) *Attorney, Agent, or Firm* — Cantor Colburn LLP

(57) ABSTRACT

The present invention relates to a composition comprising caspofungin or a pharmaceutical acceptable salt thereof and succinate or lactate as a buffering agent.

19 Claims, 2 Drawing Sheets

CASPOFUNGIN COMPOSITION

CROSS-REFERENCE TO RELATED APPLICATIONS

This application is a continuation of U.S. patent application Ser. No. 13/237,193 filed on Sep. 20, 2011, which claims the benefit of U.S. Provisional Patent Application Ser. No. 61/384,333, filed Sep. 20, 2010, which is incorporated by reference herein in its entirety.

FIELD OF THE INVENTION

The present invention relates to a composition comprising caspofungin or a pharmaceutical acceptable salt thereof and succinate or lactate as a buffering agent.

BACKGROUND

Caspofungin (CAS 162808-62-0) is the first of a new class of semi-synthetic antifungal agents belonging to the class of echinocandins. It may be represented by the formula I

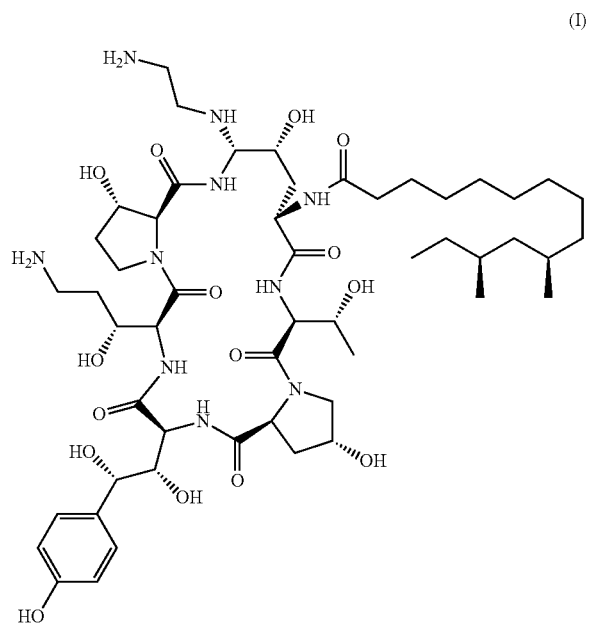 [SMILES: CC[C@H](C)C[C@H](C)CCCCCCCCC(=O)N[C@H]1C[C@@H](O)[C@@H](NCCN)NC(=O)[C@@H]2[C@@H](O)CCN2C(=O)[C@H]([C@H](O)CCN)NC(=O)[C@H]([C@H](O)[C@@H](O)c2ccc(O)cc2)NC(=O)[C@@H]2C[C@@H](O)CN2C(=O)[C@H]([C@@H](C)O)NC1=O]

(I)

Caspofungin is commonly prepared by synthetic derivatisation of pneumocandin $B_0$ which is obtained by fermentation of the fungus *Glarea lozoyensis*. The antifungal activity of caspofungin is due to its inhibition of the biosynthesis of $\beta$-(1,3)-D-glucan, an integral component of the fungal cell wall. It is used for the treatment of invasive aspergillosis in patients who are refractory to or intolerant of other therapies, as well as empirical therapy for presumed fungal infections in febrile, neutropenic patients.

Caspofungin as a compound is claimed in the patent U.S. Pat. No. 5,378,804 issued to Merck & Co.

U.S. Pat. No. 5,952,300 discloses a composition for treating and/or preventing fungal infections comprising caspofungin and the pharmaceutically active salt thereof, a pharmaceutically active amount of an acetate buffer and a pharmaceutically acceptable amount of excipients such as a sucrose/mannitol mixture to form a lyophilized cake.

A lyophilized caspofungin product is available on the marketed as its diacetate salt by Merck & Co., under the trade name Cancidas® (RLD product). Cancidas® contains in addition to the active ingredient caspofungin diacetate, acetic acid, sodium hydroxide, sucrose and mannitol. Before administration to a patient, the lyophilized product is reconstituted by adding a diluent and the desired amount of the diluted mixture is transferred to infusion bag to be administered to the patient in need thereof.

A well known problem with caspofungin compositions prepared for reconstitution prior to administration to the patient, is that the compound is highly unstable resulting in the formation of various degradation products such as e.g. hydrolysis products (impurity B) and dimerization products (impurity C). There will also be impurities present in the composition being formed during the fermentation of the starting material and which have passed along through the synthesis of caspofungin. The main impurity originating from the fermentation is the serine analogue of caspofungin having the formula as shown in WO 2009/158034

In addition to the above mentioned degradation impurities and impurities formed during preparation of known caspofungin compositions, further non-characterised impurities are also present. The mechanisms behind the formation of the impurities are not fully understood. However, it is known that the buffer system used when preparing the composition may increase the degradation product formation during preparation and storage. In U.S. Pat. No. 5,952,300 it is, for example, stated that the use of tartrate buffer resulted in undesired degradation products. The solution to the degradation problem according to the teaching of U.S. Pat. No. 5,952,300 is the use of an acetate buffer.

Various other strategies are also known to avoid degradation and improve the stability of caspofungin compositions. For example, in WO 2009/002481, a lyophilized caspofungin composition comprising in addition to caspofungin diacetate and an acetate buffer, one or more non-reducing sugars such as trehalose, sucrose, raffinose, or sorbitol or combinations thereof is disclosed.

In WO 2008/012310, a caspofungin composition is disclosed comprising, in addition to a pharmaceutically acceptable salt of caspofungin and excipients, only very low levels of a buffering agent, or which is free of a buffering agent.

Although various solutions to the impurity problem are suggested in the prior art, there is still a need for a caspofungin composition with improved stability in respect of the formation of impurities during storage.

SUMMARY OF THE INVENTION

The present inventors have surprisingly found that an antifungal composition according to the present invention comprising caspofungin or a pharmaceutically acceptable salt thereof, one or more pharmaceutically acceptable excipients and including succinat or lactate as a buffering agent, is stable resulting in reduced formation of degradation products during storage.

The present invention therefore provides a composition comprising a) a pharmaceutically effective amount of caspofungin or a pharmaceutically acceptable salt thereof; b) a pharmaceutically acceptable amount of one or more pharmaceutically acceptable excipients effective to form a lyophilized cake; and c) a pharmaceutically effective amount of a buffering agent selected from the group consisting of lactate and succinate.

According to one aspect of the invention, the pharmaceutically acceptable salt of caspofungin is an acetate salt.

According to another aspect, the composition according to the invention comprises a diacetate salt of caspofungin.

According to yet another aspect of the invention, the buffering agent of the composition is succinate. According to yet another aspect of the invention, the buffering agent of the composition is lactate.

Furthermore, a composition is provided wherein the excipients is selected from the group consisting of stabilisers, diluents, antioxidants, or preservatives. According to one aspect, the stabilisators are selected from the group consisting of sucrose and mannitol; or a combination thereof.

According to a further aspect of the present invention, a compositing is provided comprising a) pharmaceutically acceptable amount of caspofungin or a pharmaceutically acceptable salt thereof; b) about 10-200 mg/ml of one or more pharmaceutically acceptable excipients effective to form a lyophilized cake; and c) a pharmaceutically effective amount of lactate or succinate providing a pharmaceutically acceptable pH.

According to one embodiment, the composition of the invention comprises an amount of caspofungin or a salt thereof corresponding to about 42 mg/ml caspofungin. According to yet another embodiment, the composition of the invention comprises about 46 mg/ml diacetate salt of caspofungin; about 30 mg/ml sucrose and about 20 mg/ml mannitol; and about 1.5 mg/ml succinate or about 1.15 mg/ml lactate.

The present invention furthermore provides a process for making a caspofungin composition according the invention comprising the steps of a) mixing an aqueous solution comprising a pharmaceutically acceptable amount of one or more excipients with a pharmaceutically effective amount of a buffering agent selected from the group consisting of lactate and succinate; b) optionally adjusting the pH by adding a base to obtain a pharmaceutically acceptable pH; c) adding to the mixture of a) a pharmaceutically acceptable amount of caspofungin or a pharmaceutically acceptable salt thereof; d) optionally adjusting the pH by adding a base to obtain a pharmaceutically acceptable pH; and e) filtering the solution obtained in d).

The mixing of the solutions of step a) of the above process may be performed in any order. Thus, according to one embodiment, a process is provided wherein step a) is performed by firstly preparing an aqueous solution comprising a pharmaceutically effective amount of a buffering agent selected from the group consisting of lactate and succinate; then adding to the said solution of buffering agent a pharmaceutically acceptable amount of one or more excipients dissolved in water. According to another embodiment, a process is provided wherein step a) is performed by firstly dissolving a pharmaceutically acceptable amount of one or more excipients in water; then adding to said solution of excipient(s) a pharmaceutically effective amount of a buffering agent selected from the group consisting of lactate and succinate.

According to one embodiment, the pH of step b) of the present invention is adjusted to 5.0-5.7. According to another embodiment, the pH of step d) of the present invention is adjusted to about 6.

According to one embodiment, a caspofungin salt, preferably caspofungin diacetate, is added in step c) of the process.

The present invention also provides a lyophilized formulation which consists of a composition which prior to lyophilization corresponds to a composition according to present invention.

The present invention furthermore provides a formulation for parenteral administration consisting of a lyophilized formulation according to the invention, wherein said lyophilized formulation is dissolved in a pharmaceutically acceptable reconstitution solution suitable for parenteral administration to a patient in need thereof. The pharmaceutically acceptable reconstitution solution may e.g. be selected from the group consisting of distilled or sterile water commonly used for injections, physiologic saline, and bacteriostatic water.

According to yet another aspect of the invention, a kit is provided comprising a first container comprising the lyophilized formulation according to the invention and a second container comprising a parenterally acceptable solvent for reconstitution thereof, and optionally a container comprising means for administrating the reconstituted solution to a patient in need thereof.

The reconstituted formulation according to the present invention may preferably be used in a method for treating or preventing a fungal infection comprising parenterally administering to a patient in need thereof, e.g. wherein the administration is performed by infusion or injection.

The present invention finally provides a use of a composition according to the invention for the preparation of a formulation for parenteral administration for the treatment or prevention of fungal infection, such as infections caused by a fungus belonging to the species *Candida* or *Aspergillus*, such as e.g. infections is caused by a fungus belonging to the species infection is caused by *C. albicans, C. tropicalis, C. krusei, C. glabrata, A. fumigatus, A. flavus* and *A. nigerc*. A method according to any of the claims 15-16, for the treatment or prevention of fungal infection, wherein the infections is caused by a fungus belonging to the species *Candida* or *Aspergillus*.

DETAILED DESCRIPTION OF THE INVENTION

Figure 1:
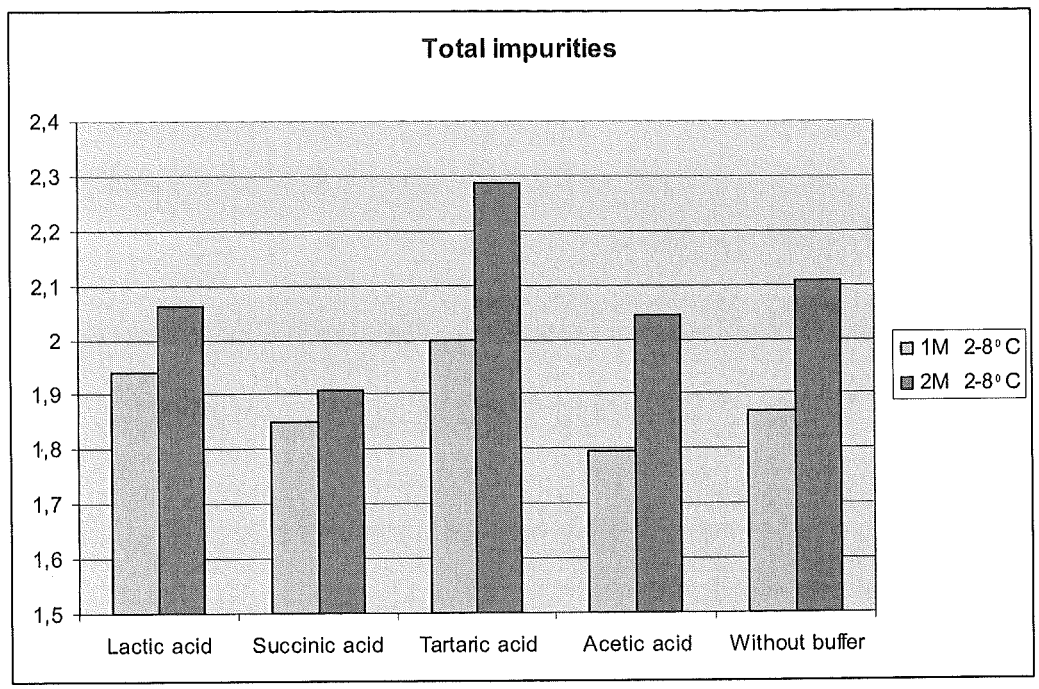
FIG. 1 shows the change in the amount of the total impurities in the lyophilized formulations prepared according to example 1 after storage in 1 month (1M) and 2 months (2M), respectively, i.e., caspofungin composition comprising caspofungin diacetate, sucrose, mannitol and as buffering agent either lactate, succinate, tartrate or acetate, and as control, a composition as above not comprising a buffering agent.

The present invention will now be described in more detail with reference to figures and examples. The following description and examples intend to illustrate the present invention, and should in no way be considered limiting. Furthermore, the skilled person will acknowledge that various modifications may be introduced without departing from the scope of the invention. Accordingly, other embodiments of the present invention which are within the abilities of the skilled person are to be understood to be within the scope of the claims.

The term "caspofungin" as used herein means caspofungin free base known under the CAS number 162808-62-0. The composition of the present invention may comprise caspofungin or a pharmaceutical acceptable salt thereof. The term "pharmaceutically acceptable salts of caspofungin" as used herein means any non-toxic salts of caspofungin. The skilled person is well known with suitable organic or inorganic acids that may be used to form salts of caspofungin, including mono-, di- and tri acid forms. For example, pharmaceutically acceptable acid addition salts may be formed using acids such as hydrochloric, hydrobromic, sulphonic, phosphoric, maleic, malic, lactic, citric, acetic, tartaric, propionic, succinic, oxalic, glutamic, pamoic acid etc. Also other acids well known to the skilled person in respect of forming pharmaceutically active salts may be used. Reference is inter alia made to Berge et a., 1977, "Pharmaceutical salts", J. Pharm. Sci., 66(1), page 1-19. Several pharmaceutical acceptable salts of caspofungin are furthermore known from e.g. U.S. Pat. No. 5,952,300, and WO 2008/12310.

According to one aspect of the invention, a lyophilized formulation is provided comprising the acetate salt of caspofungin. According to yet another aspect of the invention, a lyophilized formulation is provided comprising the diacetate salt of caspofungin. An acetate salt of caspofungin, such as a diacetate salt of caspofungin may be prepared as disclosed in U.S. Pat. No. 5,952,300.

The term "lyophilized formulation" as used herein means a formulation being prepared by lyophilization/freeze drying of a mixture comprising a pharmaceutically effective amount of caspofungin or a pharmaceutically acceptable salt thereof; a pharmaceutically acceptable amount of one or more pharmaceutically acceptable excipients; and a pharmaceutically acceptable amount of a buffering agent selected from the group consisting of lactate and succinate. The lyophilized formulation may be comprised in lyophilization vials suitable for transport and handling, and for the providing of a reconstituted formulation ready to be administered to a patient in need thereof.

The one or more pharmaceutically acceptable excipients of the composition of the invention may be any pharmaceutically acceptable excipients suitable for formation of a lyophilized cake. The one or more pharmaceutically acceptable excipients may further be well known diluent(s) or carrier(s) suitable for parenteral administration and which are well known to the skilled person. Suitable excipients that may be comprised in a composition according to the present invention may be selected from the non-limiting list of the group consisting of stabilizers, diluents, antioxidants, preservatives and the like. For example, a non-limiting list of stabilizers useful in the composition of the present invention comprises sucrose, trehalose, raffinose, sorbitol and/or mannitol.

According to one aspect of the invention, the composition of the present invention comprises sucrose or mannitol, or a combination thereof. Based on the teaching of the present invention, the skilled person will be able to select the appropriate excipients and amounts thereof for the manufacturing of a composition according to the present invention.

According to the present invention, the composition of the invention comprises as a buffering agent lactate or succinate. The buffering agent can be obtained by either dissolving the salt or the acid form of the buffering agent into water e.g. lactate-salt or lactic acid or succinate-salt or succinic acid. When preparing the composition of the present invention, the buffer agent may also be used in solid form, such as by adding succinic acid or lactic acid into a solution of excipients. Said buffering agent is used in a pharmaceutically effective amount ensuring the providing and maintenance of a pharmaceutically acceptable pH value. More specifically, a pharmaceutically acceptable pH value within the meaning of the present invention is in the range of about 5 to about 8, such as e.g. about 5.5-7.5, such as about 5.5-7.0, such as about 5.5-6.5, such as e.g. about 6.0.

The composition of the present invention results in reduced formation of total impurities during storage of a lyophilized formulation prepared therefrom compared with lyophilized formulations based on an acetate buffer system or lyophilized formulations known in the art prepared from a composition not comprising a buffering agent. The term "total impurities" as used herein means the total amount of impurities commonly present in a pharmaceutically acceptable caspofungin product or a pharmaceutically active caspofungin salt prepared according to method for preparing caspofungin or a salt thereof well known to the skilled person in the art. The total amount of impurities present may be measured by HPLC-analysis. The change in the total amount of impurities during storage may be presented as the sum of the area percentage of the total amount of impurities in a formulation to be analysed. The persons skilled in the art are familiar with various applicable HPLC devices and methods for measuring the formation of impurities during storage.

The composition according to the present invention is prepared by dissolving and mixing the ingredients, filtering the obtained mixture, and after transferring the solution to suitable vials. The so obtained solution is lyophilized to obtain a lyophilized cake. Lyophilization, or freeze-drying, is a dehydration process typically used to preserve unstable materials or make a material more convenient for transport. It is commonly used within the pharmaceutical industry and involves freezing of the material in question and reduction of the surrounding pressure, adding enough heat to allow the frozen water in the material to sublime and thus be removed from the resulting lyophilized product. The skilled person is well known with the various means and devices available for lyophilization within the pharmaceutical area. The composition according to the present invention is preferably lyophilized in pharmaceutically acceptable vials according to the method of the present invention to obtain a lyophilized cake of the composition of the present invention.

The so obtained lyophilized formulation contained in a lyophilization vial may later be reconstituted to its original form prior to administration of the reconstituted solution to a patient in need thereof. The term "formulation for parenteral administration" as used herein means liquid formulation comprising a pharmaceutically effective amount of the caspofungin composition according to the present invention, and wherein said composition have been dissolved in or mixed with one or more pharmaceutically acceptable reconstitution solutions.

The reconstitution may be performed by dissolving the lyophilized product in a pharmaceutically acceptable reconstitution solution. The skilled persons in the art are familiar with various solutions useful for the reconstitution of a lyophilized caspofungin formulation. A pharmaceutically acceptable reconstitution solution is e.g. distilled or sterile water commonly used for injections, physiologic saline, or bacteriostatic water for injection. Bacteriostatic water commonly comprises bacteriostatic compounds as preservatives, such as e.g. benzyl alcohol.

A pharmaceutically acceptable amount of the reconstituted formulation may then be transferred to means suitable for parenteral administration, such as e.g. intramuscular, subcutaneous, intravenous, intra-peritoneal administration.

The reconstituted formulation according to the present invention may be used to treat or prevent infections in a patient. The formulation may inter alia be used to prevent or fight an infections caused by fungus belonging to the *Candida* species and *Aspergillus* species. More specifically, said formulation may be used to treat or prevent infections caused by e.g. *C. albicans, C. tropicalis, C. krusei, C. glabrata, A. fumigatus, A. flavus* and *A. niger*. The present invention therefore also provides a method for the treatment or prevention of fungal infection, such as the infections cause by the above mentioned species.

EXAMPLES

Preparation of Caspofungin Diacetate Formulations

A caspofungin composition was prepared by firstly dissolving mannitol in water, then adding sucrose and succinic acid. After the addition of succinic acid, pH was determined and 0.1 M NaOH was then added to adjust the pH to 4.0. To the so-obtained solution, caspofungin diacetate corresponding to 42 mg/ml caspofungin was added. The pH of the so obtained solution was then again adjusted to pH 6.1 with 0.1 M NaOH, and the solution was mixed by stirring.

The volume of the solution was adjusted to 400 ml by adding water acceptable for injection, and filtered through a 0.22 μm filter. The solution was thereafter transferred to 10 ml lyophilization vials and stopped with sterile rubber stoppers. The solution was then subjected to lyophilization. The preparation of the composition, except during freeze drying, was performed at a temperature of 2-8° C.

The amount of the various ingredients of the composition was as listed in the below table 1.

TABLE 1

| Caspofungin diacetate | 46.58 mg/ml |
| Sucrose | 30.00 mg/ml |
| Mannitol | 20.00 mg/ml |
| Succinic Acid | 1.50 mg/ml |

Similar formulations with the difference that lactic acid, tartaric acid, citric acid or acetic acid was used in stead of succinic acid were prepared according to the above method. In addition, a formulation not comprising any buffering agent was prepared as a control.

The lyophilized cakes obtained were further subjected to analysing to determine the stability in respect of formation of impurities during storage (example 4). However, due to unexpected and undesirable precipitation of caspofungin when using citric acid as a buffering agent, said composition was abandoned for further analysing Preparation of Caspofungin Diacetate Formulation with Succinic Acid A caspofungin composition was prepared by firstly dissolving succinic acid in water, then the pH of the solution was adjusted to about 5.5-5.7 by adding NaOH solution. Then secondly sucrose and mannitol were added to the above solution. If needed the pH was again adjusted to about 5.5-5.7 by addition of NaOH. To the so obtained solution, caspofungin diacetate was added. After complete dissolution the pH was again adjusted with NaOH to reach about 5.9-6.1. The solution volume was then adjusted to final value to reach the concentrations given in Table 1.

The so obtained composition was filtered through a 0.22 μm filter and thereafter transferred to 10 ml lyophilization vials and stopped with sterile rubber stoppers. The solution was then subjected to lyophilization. The preparation of the composition, except during freeze drying, was performed at a temperature of 2-8° C.

Preparation of Caspofungin Diacetate Formulation with Lactic Acid

A caspofungin composition was prepared by firstly dissolving lactic acid in water, then the pH of the solution was adjusted to about 5.0 by adding NaOH solution. Then secondly sucrose and mannitol were added to the above solution. If needed the pH was again adjusted to about 5.0 by addition of NaOH. To the so obtained solution, caspofungin diacetate was added. After complete dissolution the pH was, if needed, adjusted with NaOH to reach about 6.3. The solution volume was then adjusted to final value to reach the concentrations given in Table 2 below.

The so obtained composition was filtered through a 0.22 μm filter and thereafter transferred to 10 ml lyophilization vials and stopped with sterile rubber stoppers. The solution was then subjected to lyophilization. The preparation of the composition, except during freeze drying, was performed at a temperature of 2-8° C.

The amount of the various ingredients of the final composition was as listed in the below table 2.

TABLE 2

| Caspofungin diacetate | 46.58 mg/ml |
| Sucrose | 30.00 mg/ml |
| Mannitol | 20.00 mg/ml |
| Lactic Acid | 1.14 mg/ml |

Analysis of Stability of Caspofungin Compositions

The formulations prepared according to example 1, example 2 and example 3 were stored in the lyophilized state at 2-8° C. for 1, 2 and 3 months, respectively, before stability testing. Prior to testing, the lyophilized material was dissolved in a pharmaceutically acceptable reconstitution solution. The so obtained solutions where then analysed by HPLC according to standard methods well known to the skilled person in the art.

The results of the stability testing, including 1 and 2 months data, of the composition prepared according to example 1 are shown in FIG. 1.

Figure 2:
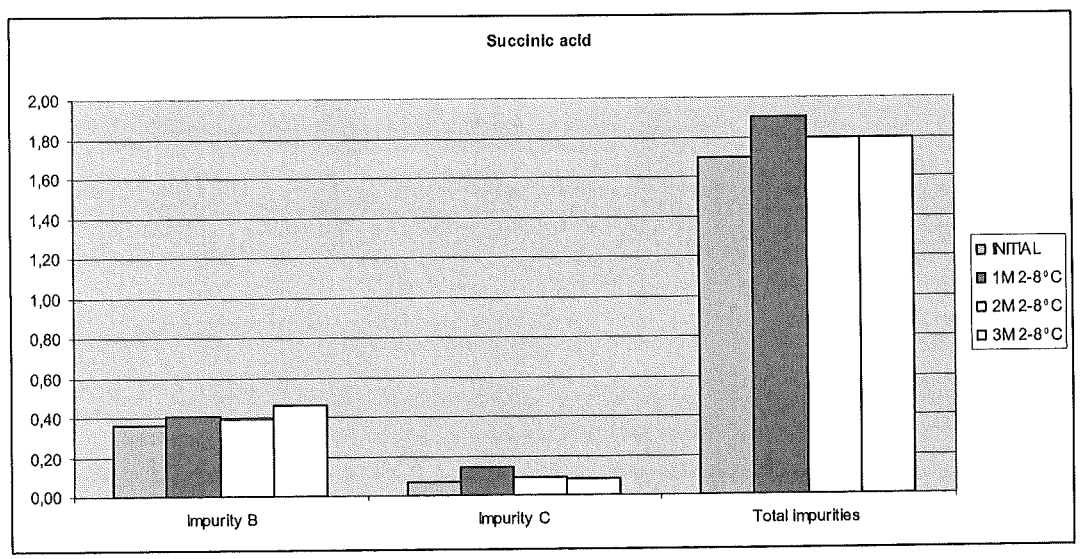
FIG. 2 shows the changes in impurity B (hydrolysis degradation product), Impurity C (dimerization product) and the total amounts of impurities in the lyophilized formulation prepared according to example 2 after storage in 1 month (1M), 2 months (2M) and 3 months (3M).

The results of the stability testing of the composition prepared according to example 2 are shown in FIG. 2.

Figure 3:
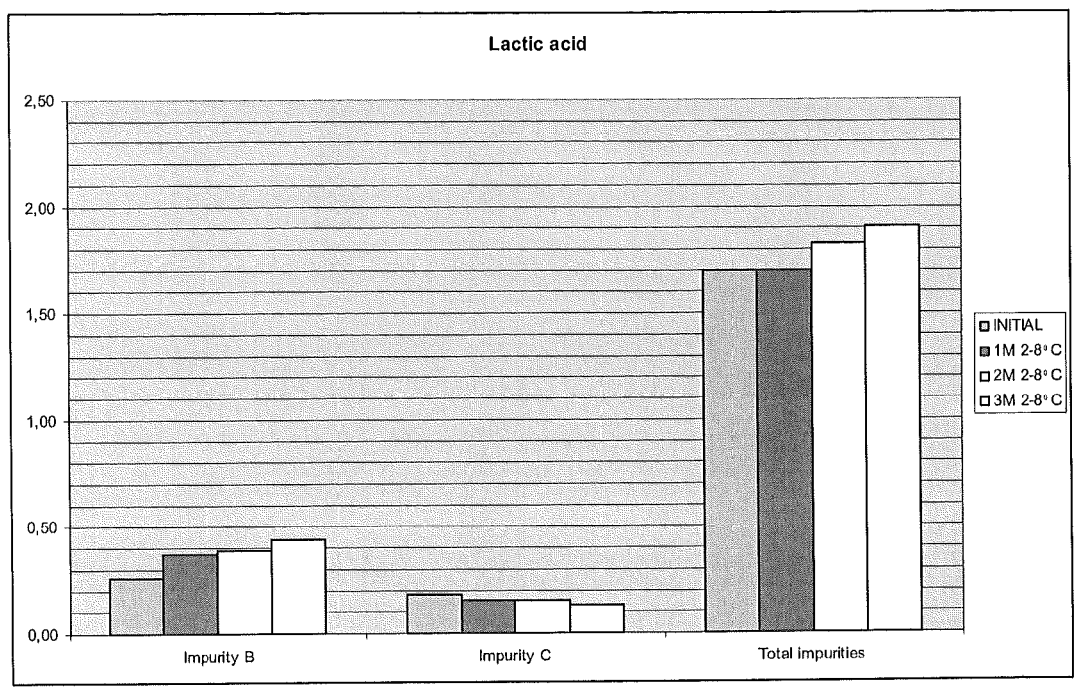
FIG. 3 shows the changes in impurity B (hydrolysis degradation product), Impurity C (dimerization product) and the total amounts of impurities in the lyophilized formulation prepared according to example 3 after storage in 1 month (1M), 2 months (2M) and 3 months (3M).

The results of the stability testing of the composition prepared according to example 3 are shown in FIG. 3.

Surprisingly, the stability testing according to FIG. 1 revealed that a lyophilized formulation based on a composition prepared using succinate or lactate as a buffering agent showed lower formation of total impurities compared with the compositions comprising acetate or tartrate. The fact that acetate seems not to be superior in respect of formation of the impurities determined is surprising taking into account the teaching of the prior art. As mentioned above, U.S. Pat. No. 5,952,300 teach that the use of tartrate buffer results in the formation of undesired degradation product in contrast to acetate buffer. It is furthermore surprisingly observed that the amount of impurities increase during storage when no buffering agent is added, contrary to the teaching of WO2008/12310.

When we compare the composition prepared according to example 2 and example 3 above with the product sold in the market by Merck (RLD) we get the following data regarding levels of impurities, see table 3.

TABLE 3

| Composition example 2 | Composition example 3 | RLD |
|---|---|---|
| Impurity B (%) 0.39 | 0.44 | 0.38 |
| Impurity C (%) 0.09 | 0.13 | 0.17 |
| Total impurities 1.8 | 1.9 | 2.1 |

The results in table 3 again shows that the use of acetate buffer in the composition is not superior compared with for instance succinate buffer or lactate buffer which is surprising taking into account the teaching of the prior art.

The invention claimed is:

1. A composition consisting of:
    a) a pharmaceutically effective amount of an acetate salt of caspofungin;
    b) a pharmaceutically acceptable amount of one or more pharmaceutically acceptable excipients effective to form a lyophilized cake; and
    c) a pharmaceutically effective amount of a succinate buffering agent.

2. The composition according to claim 1, wherein the one or more excipients is selected from the group consisting of diluents, antioxidants, and preservatives.

3. The composition according to claim 1, wherein the excipient is selected from the group consisting of sucrose, mannitol; and a combination thereof.

4. The compositing according to claim 1, wherein the composition consists of:
    a) a pharmaceutically acceptable amount of caspofungin or a pharmaceutically acceptable salt thereof;
    b) about 10-200 mg/ml of one or more pharmaceutically acceptable excipients effective to form a lyophilized cake;
    c) a pharmaceutically effective amount of succinate effective to provide a pharmaceutically acceptable pH.

5. The composition according to claim 4, wherein the composition includes an amount of caspofungin or a salt thereof corresponding to about 42 mg/ml caspofungin.

6. The composition according to claim 5, wherein the composition consists of:
    a) about 46 mg/ml diacetate salt of caspofungin;
    b) about 30 mg/ml sucrose and about 20 mg/ml mannitol; and
    c) about 1.5 mg/ml succinate.

7. A process for making a caspofungin composition according to claim 1 comprising the steps of: a) mixing an aqueous solution comprising a pharmaceutically acceptable amount of one or more excipients with a pharmaceutically effective amount of a succinate buffering agent; b) optional adjusting the pH by adding a base to obtain a pharmaceutically acceptable pH; c) adding to the mixture of a) a pharmaceutically acceptable amount of caspofungin or a pharmaceutically acceptable salt thereof; d) optional adjusting the pH by adding a base to obtain a pharmaceutically acceptable pH; e) filtering the solution obtained in d).

8. The process for making a caspofungin composition according to claim 7, wherein step a) is performed by firstly preparing an aqueous solution comprising a pharmaceutically effective amount of a succinate buffering agent; and then adding to said solution of buffering agent a pharmaceutically acceptable amount of one or more excipients dissolved in water.

9. The process for making a caspofungin composition according to claim 7, wherein step a) is performed by firstly dissolving a pharmaceutically acceptable amount of one or more excipients in water; then adding to said solution of excipient(s) a pharmaceutically effective amount of a succinate buffering agent.

10. The process according to claim 7, wherein the pH is adjusted to 5.0-5.7 in step b).

11. The process according to claim 7, wherein the pH is adjusted to about 6 in step d).

12. The process according to claim 7, wherein caspofungin diacetate is added in step c).

13. A lyophilized formulation consisting of a composition which prior to lyophilization corresponds to a composition according to claim 1.

14. The formulation for parenteral administration consisting of a lyophilized formulation according to claim 13, wherein said lyophilized formulation is dissolved in a pharmaceutically acceptable reconstitution solution suitable for parenteral administration to a patient in need thereof.

15. The formulation for parenteral administration according to claim 14, wherein the pharmaceutically acceptable reconstitution solution is selected from the group consisting of distilled water, sterile water, physiologic saline, and bacteriostatic water.

16. A kit comprising a first container comprising the lyophilized formulation according to claim 13 and a second container comprising a parenterally acceptable solvent for reconstitution thereof, and optionally a container comprising means for administrating the reconstituted solution to a patient in need thereof.

17. A method of treating or preventing a fungal infection, comprising parenterally administering to an individual in need thereof a composition according to claim 5.

18. The method according to claim 17, wherein the infection is caused by a fungus belonging to the species *Candida* or *Aspergillus*.

19. The method according to claim 18, wherein the infection is caused by a fungus belonging to the species infection is caused by *C. albicans, C. tropicalis, C. krusei, C. glabrata, A. fumigatus, A. flavus* or *A. niger*.

* * * * *